(12) United States Patent (10) Patent No.: US 12,642,952 B2
Wales et al. (45) Date of Patent: Jun. 2, 2026

(54) FLUID CONTAINER ADAPTERS

(71) Applicant: Boston Scientific Scimed, Inc., Maple Grove, MN (US)

(72) Inventors: Ryan V. Wales, Northborough, MA (US); Jeff Gray, Sudbury, MA (US); Scott E. Brechbiel, Acton, MA (US); Colby Harris, Weston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1290 days.

(21) Appl. No.: 17/480,847

(22) Filed: Sep. 21, 2021

(65) Prior Publication Data

US 2022/0096812 A1 Mar. 31, 2022

Related U.S. Application Data

(60) Provisional application No. 63/084,284, filed on Sep. 28, 2020, provisional application No. 63/084,297, (Continued)

(51) Int. Cl.
*A61B 1/015* (2006.01)
*A61B 1/00* (2006.01)
(Continued)

(52) U.S. Cl.
CPC ......... *A61M 39/14* (2013.01); *A61B 1/00121* (2013.01); *A61B 1/00128* (2013.01);
(Continued)

(58) Field of Classification Search
CPC ........ B65D 39/00; B65D 39/12; B65D 39/04; B65D 39/025; B65D 39/02;
(Continued)

(56) References Cited

U.S. PATENT DOCUMENTS 1,256,961 A * 2/1918 Welsh .................... B65D 88/54
                                                            141/338
1,420,011 A * 6/1922 Abbott .................... B67C 11/02
                                                            141/338

(Continued)

FOREIGN PATENT DOCUMENTS

EP        3440986 A1     2/2019
WO   2020150708 A2     7/2020

OTHER PUBLICATIONS

International Search Report and Written Opinion for PCT/US2021/051314, mailed Jan. 5, 2022 (12 pages).

*Primary Examiner* — Michael J Tsai
*Assistant Examiner* — Benjamin Koo
(74) *Attorney, Agent, or Firm* — Seager, Tufte & Wickhem, LLP

(57) ABSTRACT

Various embodiments are generally directed to fluid container adapters that couple with a fluid container, so to enable access to the contents of the fluid container, such as from an endoscopic system via a tubing set. Several embodiments are particularly directed to a fluid container adapter that can couple with an opening in a variety of fluid containers to place one or more tubes in fluid communication with an interior of any particular one of the variety of fluid containers.

15 Claims, 15 Drawing Sheets

Related U.S. Application Data filed on Sep. 28, 2020, provisional application No. 63/084,292, filed on Sep. 28, 2020, provisional application No. 63/084,274, filed on Sep. 28, 2020.

(51) Int. Cl.

| | |
|---|---|
| *A61B 1/005* | (2006.01) |
| *A61J 1/14* | (2023.01) |
| *A61M 39/10* | (2006.01) |
| *A61M 39/14* | (2006.01) |

(52) U.S. Cl.

CPC ........ *A61B 1/00137* (2013.01); *A61B 1/0058* (2013.01); *A61B 1/015* (2013.01); *A61J 1/1418* (2015.05); *A61J 1/1481* (2015.05); *A61M 39/10* (2013.01); *A61M 2039/1077* (2013.01)

(58) Field of Classification Search

CPC .... B65D 39/0088; B65D 39/20; A61J 1/1412; A61J 1/1418; A61J 1/1481; A61B 1/12; A61B 1/126; A61B 1/00128; B67C 2011/20; A61M 39/20

See application file for complete search history.

(56) References Cited

U.S. PATENT DOCUMENTS

| | | | | |
|---|---|---|---|---|
| 4,256,154 | A * | 3/1981 | Black | B65D 47/063 |
| | | | | 215/44 |
| 4,509,243 | A * | 4/1985 | Schneider | F16L 55/1683 |
| | | | | 29/402.09 |
| 6,152,198 | A * | 11/2000 | Nguyen | B67C 11/02 |
| | | | | 141/338 |
| 9,126,814 | B2 * | 9/2015 | Tarasoff | B67C 11/02 |
| 2006/0149131 | A1 | 7/2006 | Or | |
| 2007/0112336 | A1 | 5/2007 | Aizenfeld et al. | |
| 2012/0103466 | A1 * | 5/2012 | Castillo | B67C 11/02 |
| | | | | 141/338 |
| 2015/0210438 | A1 * | 7/2015 | Ledun | B65D 55/02 |
| | | | | 53/490 |
| 2019/0117046 | A1 | 4/2019 | Briggs | |

* cited by examiner

520

530

FLUID CONTAINER ADAPTERS

PRIORITY

The present application claims the benefit of priority under 35 U.S.C. § 119 to U.S. Provisional Application Ser. Nos. 63/084,274, 63/084,284, 63/084,292, and 63/084,297, each filed Sep. 28, 2020, the disclosures of which are incorporated herein by reference in their entirety.

FIELD

The present disclosure relates generally to adapters for fluid containers. In particular, the present disclosure relates to fluid container adapters for endoscopic systems

BACKGROUND

Endoscopy procedures that use typical endoscopes have some common functionalities available to an operator. One includes the ability to insufflate a patient by passing a fluid, such as air or carbon dioxide, through the endoscope in a controlled manner into a target luminal space. Another includes the ability to flush water across the imaging lens to clear the field of view. Yet another of the common functionalities includes the ability to irrigate the lumen to clean surfaces and aid in flushing/suctioning debris during a procedure. Oftentimes, these common functionalities, among others, are driven during a procedure by one or more fluid containers and/or sources. For example, an air pump or carbon dioxide source for insufflation, a water bottle for lens cleaning, and/or a sterile water bottle for irrigation. In some cases, a hybrid tubing set may be used to drive both lens cleaning and irrigation from a sterile water bottle. In either case, the one or more fluid containers and/or sources must be attached to the tubing set of the endoscope. It is with all of the above considerations in mind that the improvements of the present disclosure may be useful.

SUMMARY

In one aspect, the present disclosure relates to an apparatus comprising a conical member and a tensioner. The conical member may include a connector portion, a sealing portion, and one or more passages extending from the connector portion to the sealing portion. The sealing portion may comprise a collapsed configuration for insertion into a fluid container and an expanded configuration for sealing with an interior of the fluid container. The tensioner may include a coupler and be configured to couple with the connector portion of the conical member, contact an exterior of the fluid container, and bias the sealing portion into contact with the interior of the fluid container.

In many embodiments, each of the one or more passages may be configured to facilitate fluid communication between a tube and the interior of the fluid container. In several embodiments, the sealing portion may comprise an elastomeric structure to bias the sealing portion into the expanded configuration. In various embodiments, the sealing portion may comprise an elastomeric composition to bias the sealing portion into the expanded configuration.

In one or more embodiments, the connector portion may include a top of the conical member, the sealing portion may include a bottom of the conical member, and the connector portion abuts the sealing portion at a transition of the conical member. In one or more such embodiments, the top of the conical member may have a first diameter, the transition of the conical member may have a second diameter, and the bottom of the conical member may have a third diameter. In such embodiments, the first and second diameters may be smaller than the third diameter. In some such embodiments, the first and second diameters are equal.

In some embodiments, the sealing portion in the collapsed configuration may be configured for insertion into the fluid container via an opening in a neck of the fluid container and the tensioner may be configured to seal with the opening in the neck of the fluid container when coupled with the connector portion. In some such embodiments, the tensioner may include a first side including a rigid material and a second side including a flexible material configured to seal with the opening in the neck of the fluid container.

In various embodiments, the connector portion of the conical member may comprise a rigid material and the sealing portion of the conical member may comprise a flexible material. In various such embodiments, the tensioner may comprise the rigid material. In many embodiments, the sealing portion of the conical member may comprise a flexible funnel. In several embodiments, the tensioner may comprise a rigid disc. In several embodiments, the sealing portion is configured to conform to a shape of the interior of the fluid container in the expanded configuration.

In another aspect, the present disclosure relates to an apparatus comprising an umbrella seal, a connecting member, and a tensioner. The umbrella seal may include a base and a skirt. The skirt may have a conical shape, be attached about a circular portion of the base, and extend from the base in a first direction. The skirt may include a collapsed configuration for insertion of the umbrella seal into a fluid container and an expanded configuration for sealing with an interior of the fluid container. The connecting member may include a threaded portion, be attached to the base of the umbrella seal, and extend from the circular portion of the base in the first direction. The tensioner may have a threaded opening and be configured to screw onto the threaded portion of the connecting member, contact an exterior of the fluid container, and bias the skirt into contact with the interior of the fluid container. Additionally, the base of the umbrella seal and the tensioner may have one or more axially aligned passages to facilitate fluid communication between a tube and the interior of the fluid container.

In many embodiments, the skirt of the umbrella seal may be biased into the expanded configuration absent application of an external force. In several embodiments, the skirt of the umbrella seal may be biased into the collapsed configuration by an opening in the fluid container as the umbrella seal is inserted, base first, through the opening in the fluid container. In various embodiments, the skirt of the umbrella seal may be biased into the expanded configuration by the interior of the fluid container when the tensioner is screwed further onto the threaded portion of the connecting member after the tensioner contacts the exterior of the fluid container. In one or more embodiments, the skirt may include a first end coupled to the circular portion of the base and a second end comprising a flare.

In yet another aspect, the present disclosure relates to a method. The method may include one or more of: transitioning a sealing portion of a conical member from an expanded configuration to a collapsed configuration, the conical member comprising a connector portion, the sealing portion, and one or more passages extending from the connector portion to the sealing portion; inserting the sealing portion in the collapsed configuration into an interior of a fluid container, wherein the sealing portion returns to the expanded configuration when in the interior of the fluid container; and biasing the sealing portion into contact with the interior of the fluid container. In some embodiments, the method may include fastening a tensioner onto the connector portion of the conical member to bias the sealing portion into contact with the interior of the fluid container.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
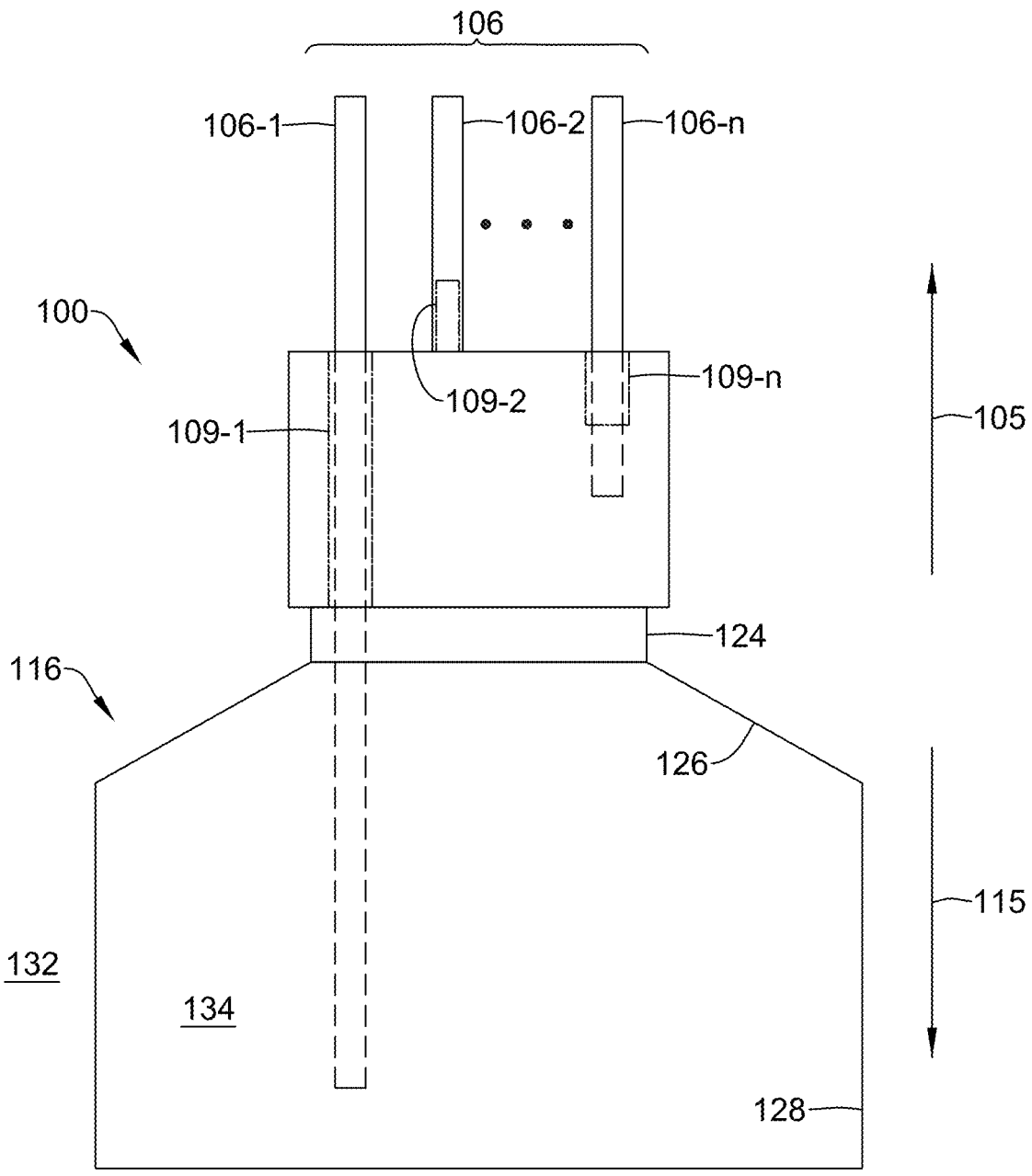
FIG. 1 illustrates a fluid container adapter in conjunction with a tube set and a fluid container according to one or more embodiments disclosed hereby.

Various embodiments are generally directed to fluid container adapters that couple with a fluid container, so to facilitate access to the contents of the fluid container, such as by an endoscopic system via a tubing set. Several embodiments are particularly directed to fluid container adapters that can couple with an opening in a variety of fluid containers to place one or more tubes in fluid communication with an interior of any particular one of the variety of fluid containers. In one embodiment, for example, a fluid container adapter may include a tensioner and a conical member with one or more passages configured to place one or more tubes in fluid communication with an interior of the fluid container. In such embodiments, a first portion of the conical member may be inserted into the interior of a fluid container via an opening in the neck of the fluid container. Further, the tensioner may attach to a second portion of the conical member to bias the first portion against the interior of the fluid container, resulting in a seal between the fluid container adapter and the fluid container. These and other embodiments are described and claimed.

Some challenges in coupling with a fluid container and gaining access to the contents of the fluid container include having a fluid container adapter that is compatible with the fluid container. For example, a fluid container adapter may include a screw cap with one or more tubes extending therethrough. In such examples, the screw cap may couple to corresponding static threads on a neck of the fluid container with the one or more tubes extending therethrough enabling the endoscopic system to access the contents of the fluid container. However, there are many different types of fluid container manufacturers that offer different fluid container designs. Further, manufacturers may offer different fluid container designs and/or periodically change or update fluid container designs. For instance, manufacturers may offer designs with different thread patterns around the world based on regional preferences or demands. This presents a challenge for manufacturers of tubing sets by requiring them to offer multiple products with customized fluid container adapters for each design. Further, product acquisition and stocking by health care facilities is complicated by necessitating they ensure that tubing sets have a fluid container adapter that is compatible with an available fluid container.

Accordingly, various embodiments of the present disclosure include fluid container adapters that widen the scope of compatibility to a variety of different fluid container designs. In many embodiments, one or more fluid container adapters of the present disclosure may provide an efficient, safe, and effective way to couple with and gain access to the contents of a multitude of fluid container designs. Enabling fluid container adapters to be compatible with different fluid container designs allows medical device companies (e.g., manufacturers of tubing sets) to offer products that are more adaptable and appeal to a broader market. Further, enabling fluid container adapters to be compatible with different fluid container designs can simplify product acquisition and stocking by health care facilities.

It may be understood that the disclosure included herein is exemplary and explanatory only and is not restrictive. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Although endoscopes and endoscopic systems are referenced herein, reference to endoscopes, endoscopic systems, or endoscopy should not be construed as limiting the possible applications of the disclosed aspects. For example, the disclosed aspects may be used in conjunction with duodenoscopes, bronchoscopes, ureteroscopes, colonoscopes, catheters, diagnostic or therapeutic tools or devices, or other types of medical devices or systems.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIG. 1 illustrates a fluid container adapter 100 in conjunction with a tube set 106 and a fluid container 116 according to one or more embodiments of the present disclosure. In one or more embodiments of the present disclosure, components of the fluid container adapters may interoperate to couple with a fluid container and facilitate access to the contents of the fluid container via a tube set, such as a tube set for an endoscopic system. In the illustrated embodiment, fluid container adapter 100 couples to fluid container 116 and places a tube set 106 of one or more tubes 106-1, 106-2, 106-*n* in fluid communication with an interior 134 of the fluid container 116. Further, at least a portion of each tube in set 106 is on an exterior 132 of the fluid container 116. In several embodiments, fluid container adapter 100 may couple to and/or seal with a portion of the fluid container 116. The components of FIG. 1 are oriented with a top 105 and a bottom 115. In some embodiments, FIG. 1 may include one or more components that are the same or similar to one or more other components of the present disclosure. Further, one or more components of FIG. 1, or aspects thereof, may be incorporated into other embodiments of the present disclosure without departing from the scope of this disclosure. Embodiments are not limited in this context.

Various embodiments disclosed hereby are directed to fluid container adapters that couple with a fluid container to enable access to the contents of the fluid container, such as from an endoscopic system via a tubing set. Several embodiments are particularly directed to a fluid container adapter that can couple with an opening in a variety of fluid containers to place one or more tubes in fluid communication with an interior of any particular one of the variety of fluid containers. In one or more embodiments, the fluid container adapter 100 may enable tube set 106 to be used in conjunction with a plurality of types and designs of fluid containers. The fluid container adapter 100 may include one or more passages 109-1, 109-2, 109-*n* to enable tubes to be placed in fluid communication with the interior 134 of the fluid container 116.

Generally, the fluid container 116 includes a neck 124, a shoulder 126, and a body 128. Additionally, the fluid container 116 may include an opening, such as at the top of the neck 124 (see e.g., FIG. 3A). In various embodiments, the fluid container adapter 100 may couple to one or more portions of the fluid container 116, such as the neck 124. In various such embodiments, the fluid container adapter 100 may block and/or seal the opening in the fluid container 116. The fluid container adapter 100 may couple to and/or seal with interior and/or exterior portions of the fluid container 116. For example, a portion of the fluid container adapter 100 may be inserted into the fluid container 116.

The fluid container adapter 100 may be constructed from a variety of materials and or components. For instance, the fluid container adapter 100 may include portions constructed from one or more materials having one or more characteristics, such as flexible, rigid, semi-rigid, semi-flexible, deformable, conformable, sealing, shape-memory, elastomeric, polymeric, and the like. In many embodiments, the fluid container adapter 100 may include layers of one or more materials. For example, the fluid container adapter 100 may include a skeleton layer of rigid materials and a skin layer of sealing material.

As previously mentioned, the fluid container adapter 100 may include one or more passages 109-1, 109-2, 109-*n* to enable tubes to be placed in fluid communication with the interior 134 of the fluid container 116. The passages 109 may place tubes in fluid communication with the interior 134 of the fluid container 116 in a variety of manners. For example, passage 109-1 may extend from the top to the bottom of the fluid container adapter 100. In another example, passage 109-2 may include a protrusion, such as with one or more Luer lock barbs, that tube 106-2 couples to. In yet another example, passage 109-*n* may extend through a portion of the fluid container adapter 100.

In some embodiments, one or more of the passages 109 may couple a tube in tube set 106 with another tubular member. In some such embodiments, the other tubular member may extend from the bottom of the passage. For example, the other tubular member may include a straw coupled to the bottom end of passage 109-*n*. In various embodiments, the other tubular member may include different characteristics than the tube in tube set 106. The other tubular member may be configured for interfacing with contents in a fluid container. For example, the other tubular member may be more flexible that the tube in tube set 106 to facilitate efficient movement of a pickup (e.g., orifice for drawing/expelling in/out fluids from the tube) to the lowest point in the fluid container. In another example, the other tubular member may be more rigid than the tube in tube set 106 to prevent kinking or curling.

In several embodiments, the fluid container adapter 100 may create a seal with one or more tubes in the tube set 106, such as by extending a tube through a passage or coupling the tube with the passage. For instance, passage 109-1 may include a lining that creates a slidable seal with tube 106-1. In some embodiments, passage 109-1 may form a fluid tight seal with the exterior of tube 106-1, the protrusion of passage 109-2 may form a fluid tight seal with the interior of tube 106-2, and passage 109-*n* may form a fluid tight seal with the exterior of tube 106-*n*. In some such embodiments, the fluid tight seals may be maintained as one or more of the tubes 106-1, 106-*n* are slid up and down in passages 109-1, 109-*n*, respectively.

Accordingly, in some embodiments, the fluid container adapter 100 may place the tube set 106 in fluid communication with the interior 134 of the fluid container 116 while keeping the interior 134 of the fluid container 116 sealed from the exterior 132. In some embodiments, the fluid container adapter 100 may maintain a slidable seal with the exterior of one or more tubes in tube set 106. For instance, the fluid container adapter 100 may maintain a fluid seal with the exterior of a tube as the tube is inserted through the fluid container adapter 100 and into the interior 134 of the fluid container 116.

In various embodiments, the tube set 106 may be used to remove fluids from and/or introduce fluids into the interior 134 of the fluid container 116. For example, tube 106-2 may be used to pump a gas (e.g., air, carbon dioxide, etc.) into the fluid container 116 and tube 106-1 may allow a liquid (e.g., water, saline, etc.) to exit the fluid container 116 as a result of the gas being pumped into the fluid container 116. In another example, tube 106-1 may be used to suck a liquid out of the fluid container 116 and tube 106-2 (or a valve built into the fluid container adapter 100) may allow gas pressure in the fluid container 116 to equalize with the atmosphere. In such other examples, a one-way valve and/or a pressure relief valve may be utilized to equalize with the atmosphere. In various embodiments, one or more of the tubes in tube set 106 may comprise an irrigation line for an endoscopic system.

As shown in the illustrated embodiment, the tubes 106-1, 106-2, 106-*n* may extend a variety of lengths into the fluid container 116. In many embodiments, the length of each of the tubes may be determined based on the function of the tube. For instance, on one hand, a vent tube may end proximate to the top 105 or couple to a passage with a fitting protruding on the exterior 132 of the fluid container adapter 100. On the other hand, a tube for removing contents, such as a liquid, from the fluid container 116 may extend to the bottom 115 of the fluid container 116. Oftentimes, a first tube of the tube set 106 may be placed in fluid communication with a first fluid (e.g., a gas) in the interior 134 of the fluid container 116 and a second tube of the tube set 106 may be placed in fluid communication with a second fluid (e.g., a liquid) in the interior 134 of the fluid container 16.

In one or more embodiments, fluid container adapter 100 may include one or more valves (e.g., one-way vales, pressure relief vales, two-way valves, and the like) to control the flow of fluids into and/or out of the fluid container 116. For example, a one-way valve may be utilized to prevent back flow into fluid container 116. Further, in some embodiments, one or more of the tubes may be coaxial. For example, a tube may be disposed coaxially with a second tube member having a larger diameter, resulting in inner and outer tubes. In some such examples, the inner and outer tubes may extend through a single passage in the fluid container adapter 100.

For this and other reasons, in many embodiments, the number of passages 109 may not directly correspond to the number of tubes in tube set 106. For example, different endoscopic systems may require different numbers of tubes in fluid communication with the interior of a fluid container. Accordingly, one or more passages may be blocked or unblocked (e.g., with a plug or cap) and/or one or more tubes may be removed or added to accommodate different endoscopic systems or different configuration of an endoscopic system. In other words, fluid container adapters can be adapted to different tube configurations and/or tube sets, such as via a variety of types of passages (e.g., passages 109-1, 109-2, 109-n).

The components of fluid container adapters disclosed hereby may be constructed from a variety of material types and compositions including one or more of polymers, elastomers, metals, alloys, shape-memory materials, rubber, silicon, plastic, composite materials, ceramics, polycarbonate, acrylonitrile butadiene styrene (ABS), high-density polyethylene (HDPE), Nylon, polyether ether ketone (PEEK), thermoplastic, stainless steel, titanium, aluminum, and the like. In some embodiments, different portions and/or components may include one or more different types, compositions, or structures of materials. For example, a shell of the fluid container adapter may be constructed from a first type of polymer and an elastic member of the fluid container adapter may be constructed from a second type of polymer with a lower durometer than the first type of polymer. In some embodiments, one or more components and/or portions of the fluid container adapter may include multiple material layers and/or embeddings, such as a semi-rigid skeletal structure.

In several embodiments, a method for utilizing one or more fluid container adapters disclosed hereby (e.g., fluid container adapter 100) may proceed with one or more of the following steps. A first end of one or more tubes may be connected to an endoscopic device or system and a second end of the one or more tubes may be coupled to a protrusion and/or extended through one or more passages in the fluid container adapter. The fluid container adapter may be coupled to a fluid container to place one or more of the tubes in fluid communication with the interior of the fluid container. In several embodiments, the fluid container adapter may seal the interior of the tubes and/or fluid container from an exterior environment. In many embodiments, the fluid container adapter may couple to a fluid container proximate an opening in the fluid container (e.g., opening in a fluid container when a cap is removed). In many such embodiments, one or more of the tubes may extend into the fluid container via the opening. In some embodiments, the fluid container adapter may attach to, cover up, or seal with the opening in the fluid container. One or more fluids may be introduced into and/or removed from the interior of the fluid container via a tube set when the fluid container adapter is coupled to the fluid container.

Figure 2A:
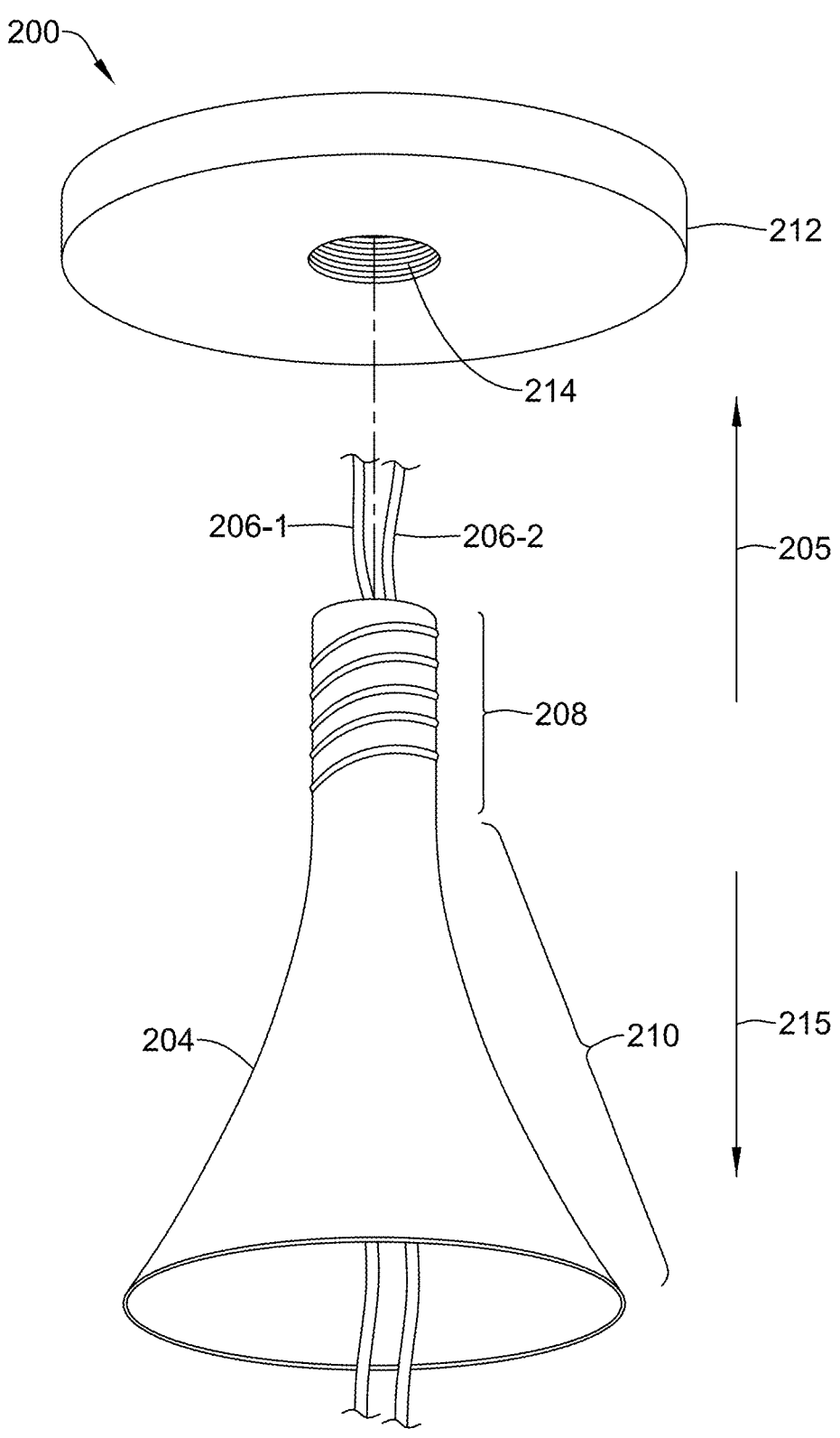
FIGS. 2A and 2B illustrate a fluid container adapter according to one or more embodiments disclosed hereby.
Figure 2B:
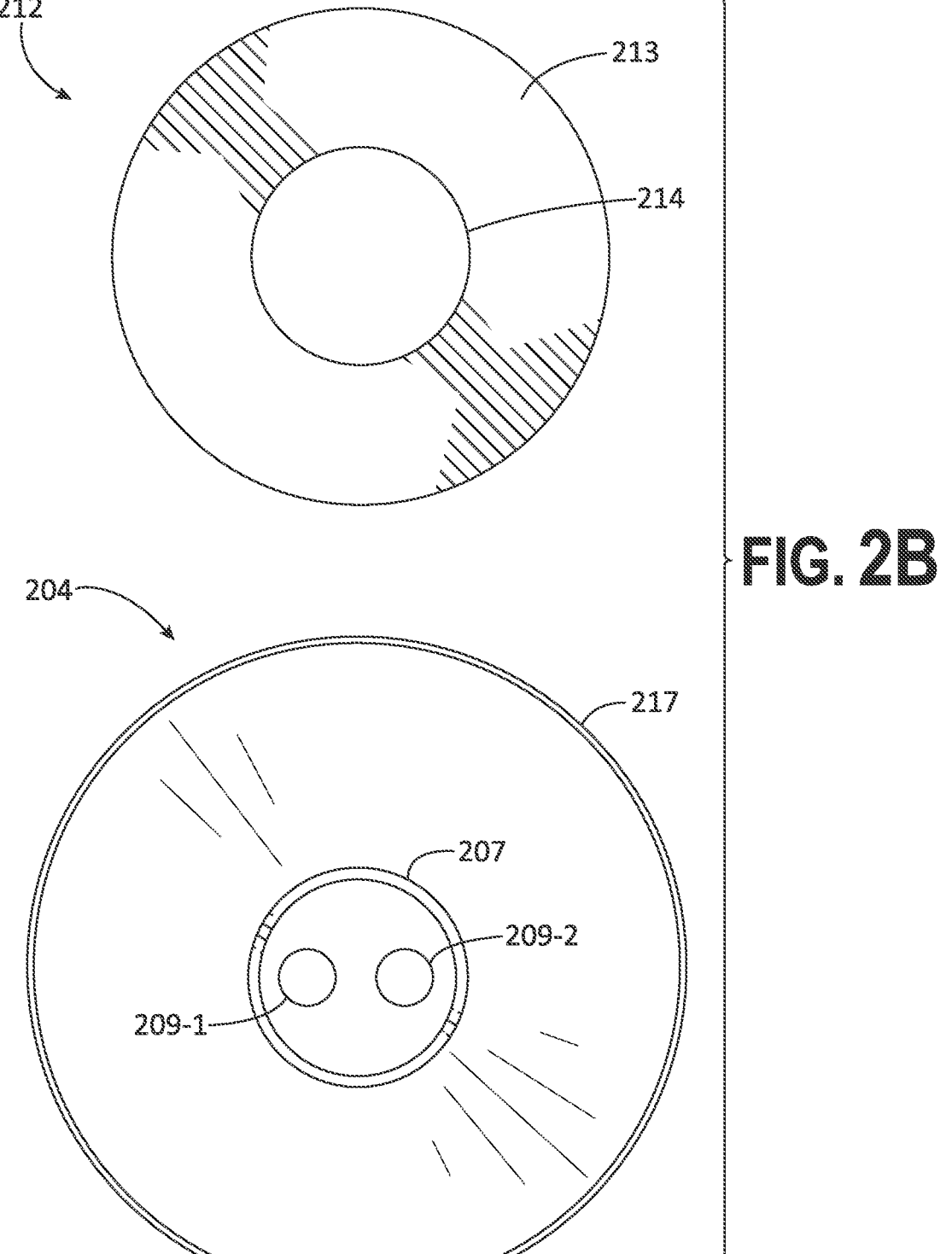

FIGS. 2A and 2B illustrate a fluid container adapter 200 according to one or more embodiments of the present disclosure. More specifically, FIG. 2A illustrates a side perspective view of the fluid container adapter 200 and FIG. 2B illustrates a top view of the fluid container adapter 200. In some embodiments, FIGS. 2A and/or 2B may include one or more components that are the same or similar to one or more other components of the present disclosure. Further, one or more components of FIGS. 2A and/or 2B, or aspects thereof, may be incorporated into other embodiments of the present disclosure without departing from the scope of this disclosure. For example, fluid container adapter 200 may be the same or similar to the fluid container adapter 100. In the illustrated embodiment, fluid container adapter 200 may include a tensioner 212 and a conical member 204. In many embodiments, the conical member 204 may be inserted into a fluid container and the tensioner 212 may bias the conical member 204 against the interior of the fluid container, oftentimes creating a seal (see e.g., FIGS. 3A-3D). The components of FIGS. 2A and 2B are oriented with a top 205 and a bottom 215. Embodiments are not limited in this context.

Various embodiments are generally directed to fluid container adapters that couple with a fluid container, so to enable access to the contents of the fluid container, such as from an endoscopic system via a tubing set. Several embodiments are particularly directed to a fluid container adapter that can couple with an opening in a variety of fluid containers to place one or more tubes in fluid communication with an interior of any particular one of the variety of fluid containers. In one embodiment, for example, a fluid container adapter may include a tensioner and a conical member with one or more passages configured to place one or more tubes in fluid communication with an interior of the fluid container. In such embodiments, a first portion of the conical member may be inserted into the interior of a fluid container via an opening in the neck of the fluid container. Further, the tensioner may attach to a second portion of the conical member to bias the first portion against the interior of the fluid container, resulting in a seal between the fluid container adapter and the fluid container.

In various embodiments, a conical member may include a sealing portion and a connector portion. In one or more embodiments, the sealing portion may be configured to seal with an internal surface of a fluid container and the connector portion may be configured to couple with a tensioner to bias the sealing portion against an internal surface of a fluid container. In the illustrated embodiment, the conical member 204 of the fluid container adapter 200 may include a sealing portion 210 and a connector portion comprising a threaded portion 208.

In various embodiments, the conical member 204 may be constructed from one or more polymers, such as an elastomer and/or a polymer, such as rubber or silicon. In some embodiments, the threaded portion 208 (or a connector portion of any embodiment) may include a first type of polymer and the sealing portion 210 may include a second type of polymer. For example, the first type of polymer may have a higher durometer than the second type of polymer. In some embodiments, conical member 204 may be composed of a variety of materials and/or layers. For example, a rigid material may be used for the threaded portion 208 (or a connector portion of any embodiment) and a flexible material may be used for the sealing portion 210.

In another example, conical member 204 may include one or more of a first layer included in the threaded portion 208 and the sealing portion 210, a second layer included in the threaded portion 208, and a third layer included in the sealing portion 210. In some such examples, the first portion may include a base layer elastomer, the second portion may include a male or female thread layer, and/or the third portion may include a sealing layer for interfacing with the interior of a fluid container.

In one or more embodiments, the diameter of the conical member 204 may be configured to conform to one or more internal features of the fluid container, such as one or more of the neck, shoulders, and body. To this end, the conical member 204 may include a variety of inner and/or outer diameters. The variety of diameters may be used to control the flexibility of portions of the conical member 204. For example, the sealing portion 210 may be more flexible than the threaded portion 208. In many embodiments, the outer diameters of the conical member 204 may be configured to generally correspond to interior surfaces of fluid containers. For example, the outer diameters of the conical member 204 may define a funnel shape.

In various embodiments, the top of the conical member 204 may have a first diameter, the transition between the threaded portion 208 and the sealing portion 210 may have a second diameter, and the bottom of the conical member 204 may have a third diameter. In some embodiments, the first and second diameters are smaller than the third diameter. In some such embodiments, the first and second diameters are equal. In various embodiments, the second diameter may be smaller than the first and third diameters. In one or more embodiments, the first diameter may be smaller than the second diameter and the third diameter.

In many embodiments, the diameter along at least a portion of the conical member 204 (e.g., the sealing portion 210) may change non-linearly. In other words, in some embodiments, the inner and/or outer diameter of a cross-section that is perpendicular to a longitudinal axis extending between the top and bottom of the conical member changes in a nonlinear manner along the longitudinal axis. For example, the inner and/or outer diameter may change in an exponential, periodic, stepwise, and/or logarithmic manner.

In various embodiments, the tensioner 212 may couple with the connector portion of conical member 204 (i.e., threaded portion 208). In some embodiments, the tensioner 212 may include a coupler configured to attach to or couple with the conical member 200. In some such embodiments, the coupler may enable the tensioner 212 to bias the sealing portion 210 of the conical member 200 against an interior of the fluid container to seal the conical member 200 with the fluid container. In the illustrated embodiment, the tensioner 212 of the fluid container adapter 200 includes a coupler comprising a threaded opening 214. The threaded opening 214 may correspond to the threaded portion 208 of the conical member 204. The tensioner 212 may be rigid or semi-rigid. In some embodiments, the tensioner 212 may comprise a disc. In various embodiments, the tensioner 212 may include a gap or a portion of the disc missing to allow tubes 206 to be positioned within the threaded opening 214. In one or more embodiments, the tensioner 212 may include a surface configured to contact and/or seal with an exterior surface surrounding an opening in the fluid container.

The sealing portion 210 of the conical member 204 may be inserted into a fluid container with the threaded portion 208 sticking out of the fluid container. The tensioner 212 may then be screwed onto the threaded portion 208 to bias the sealing portion 210 against the interior of the fluid container. In some embodiments, passage 209-1 may form a fluid tight seal with the exterior of tube 206-1 and passage 209-2 may form a fluid tight seal with the exterior of tube 206-2. In some such embodiments, the fluid tight seals may be maintained as the tubes 206 are slid up and down in the passages 209. This may be described in more detail with respect to conical member 304 and tensioner 312 with respect to FIGS. 3A-3D.

In many embodiments, the number of passages 209 may not directly correspond to the number of tubes 206. For example, different endoscopic systems may require different numbers of tubes in fluid communication with the interior of a fluid container. Accordingly, one or more passages may be blocked or unblocked (e.g., with a plug) and/or one or more tubes may be removed or added to accommodate different endoscopic systems or different configuration of an endoscopic system. In other words, fluid container adapters can be adapted to different tube configurations and/or tube sets.

Figure 3A:
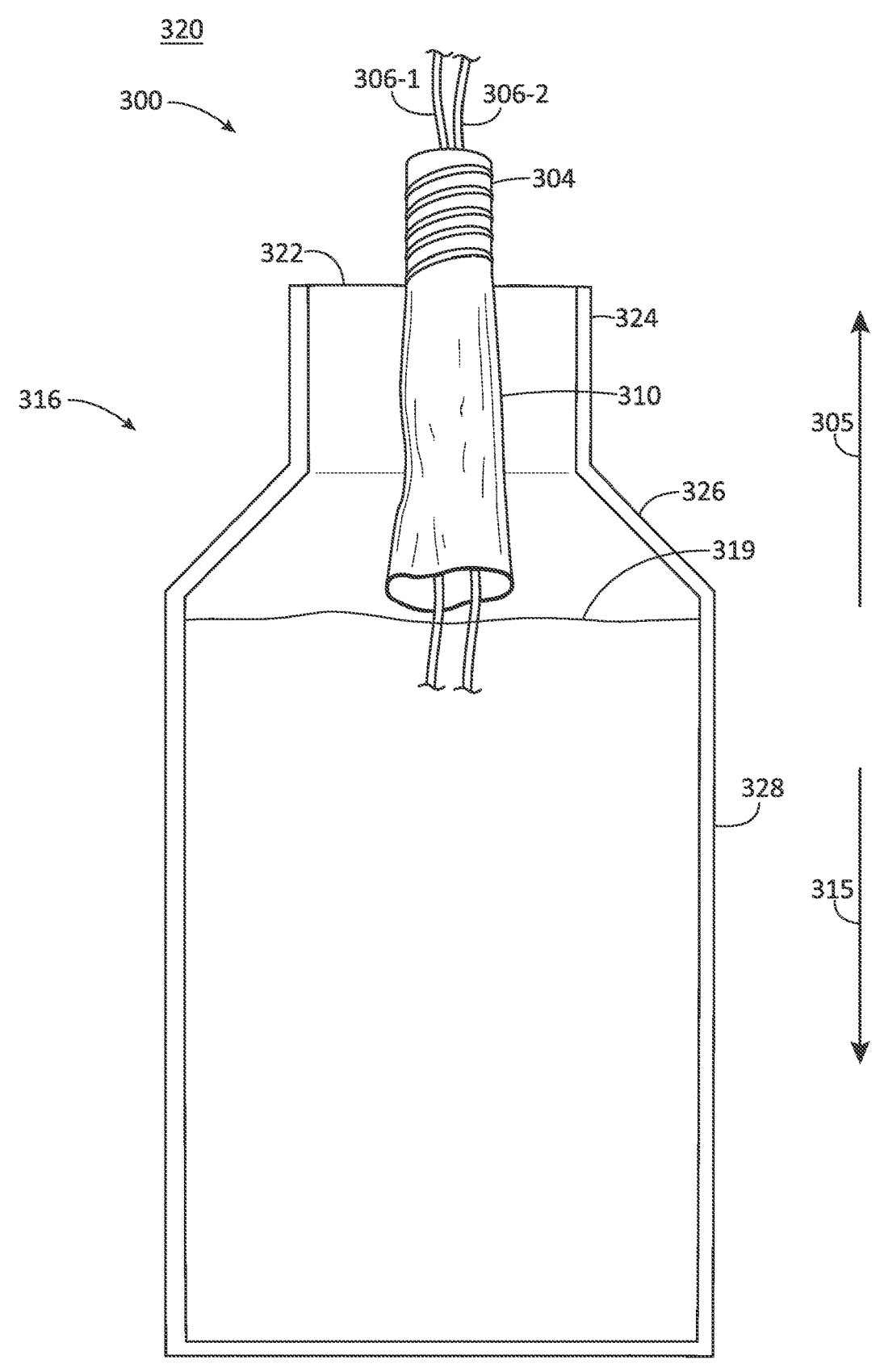
FIGS. 3A-3D illustrate exemplary aspects of a fluid container adapter in conjunction with a fluid container according to one or more embodiments disclosed hereby.
Figure 3B:
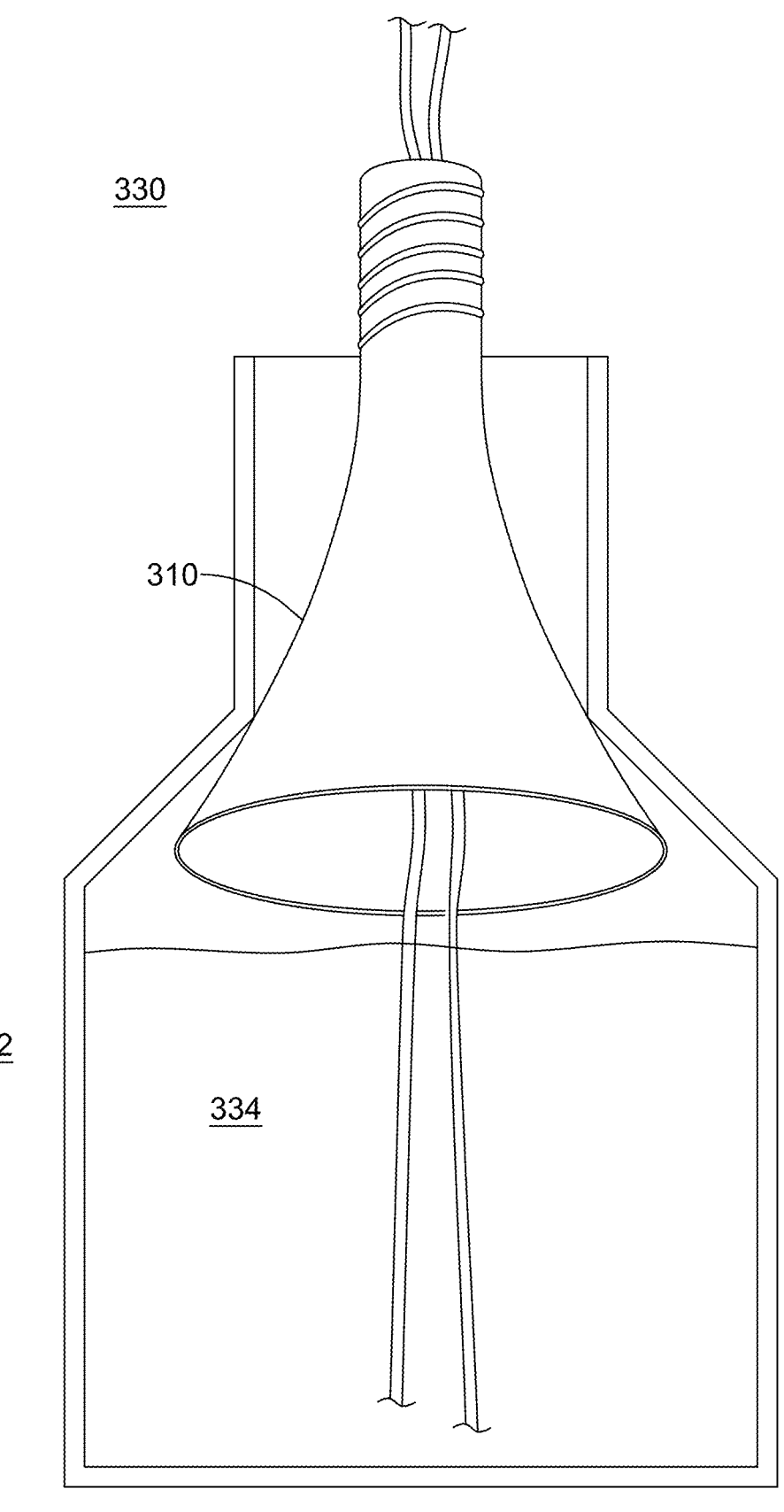
Figure 3C:
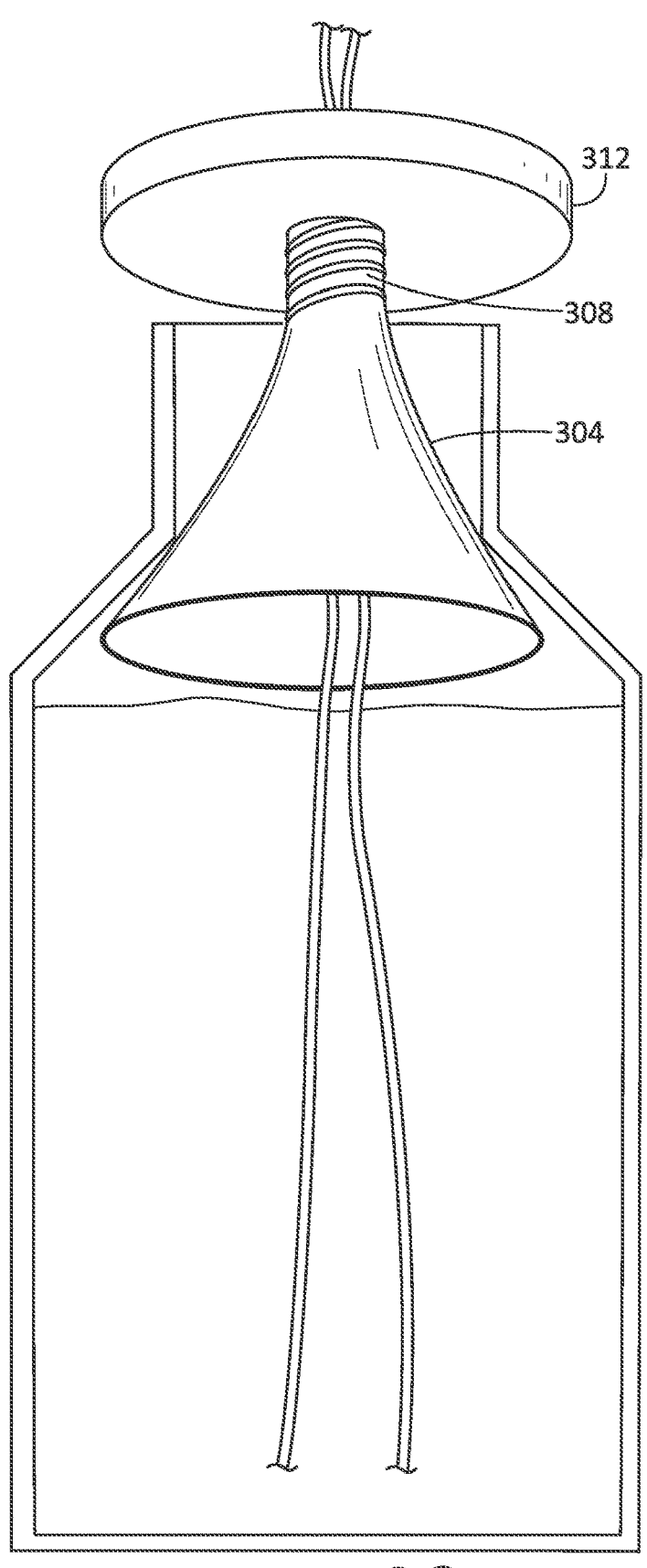
Figure 3D:
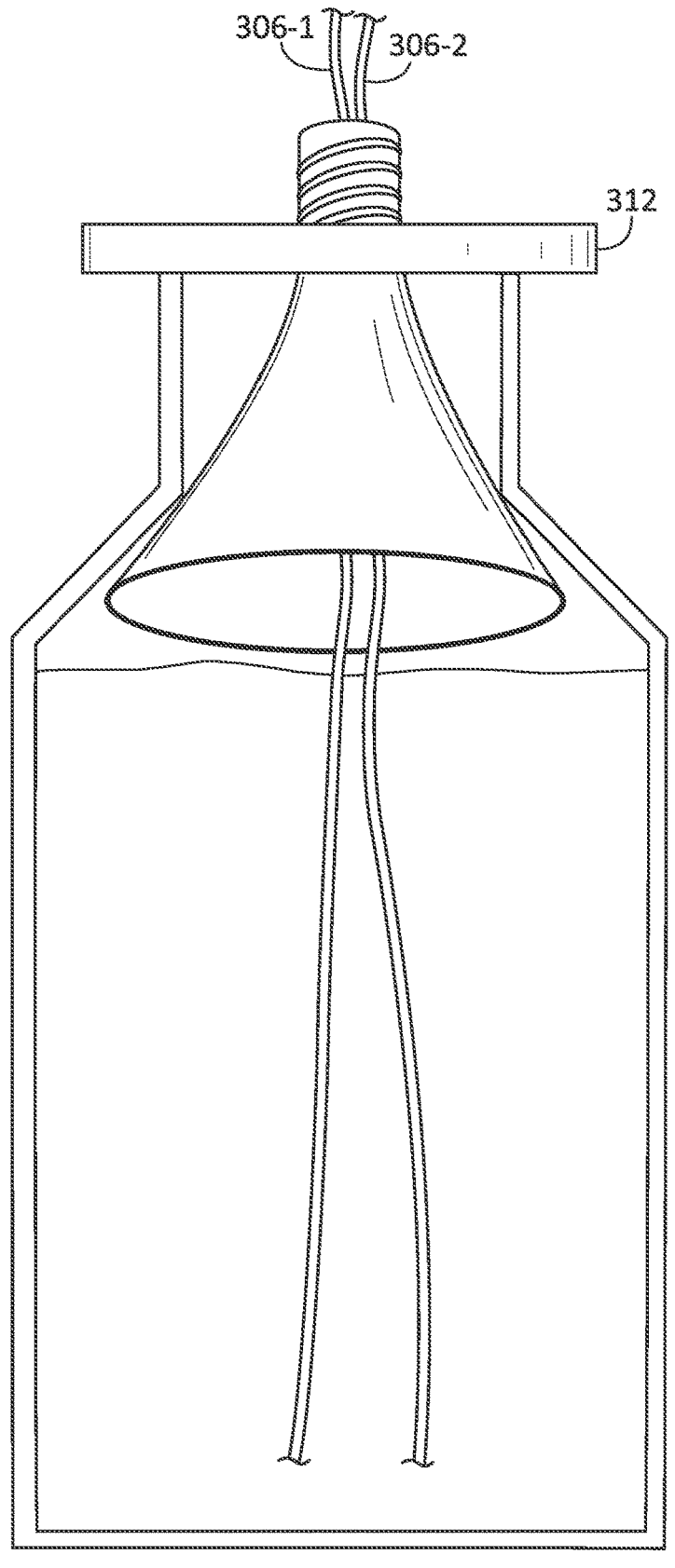

FIGS. 3A-3D illustrate various aspects of a fluid container adapter 300 in conjunction with a fluid container 316 according to one or more embodiments of the present disclosure. More specifically, FIG. 3A illustrates insertion of a sealing portion 310 (in a collapsed configuration 320) of the fluid container adapter 300, into an interior 334 of the fluid container 316. FIG. 3B illustrates the sealing portion 310 (in an expanded configuration 320) disposed in the interior 334 of the fluid container 316. FIG. 3C illustrates attaching a tensioner 312 of the fluid container adapter 300 to a threaded portion 308 of the fluid container adapter 300. FIG. 3D illustrates biasing the sealing portion 310 of the fluid container adapter 300 into contact with the interior 334 of the fluid container 316. In some embodiments, FIGS. 3A-3D may include one or more components that are the same or similar to one or more other components of the present disclosure. Further, one or more components of FIGS. 3A-3D, or aspects thereof, may be incorporated into other embodiments of the present disclosure without departing from the scope of this disclosure. For example, fluid container adapter 300 may be the same or similar to the fluid container adapter 200. Embodiments are not limited in this context.

Fluid container adapter 300 may include tensioner 312 and conical member 304 with sealing portion 310. Tubes 306-1, 306-2 extend through the conical member 304 via passages (not illustrated). In many embodiments, the sealing portion 310 of conical member 304 may be inserted into fluid container 316 and the tensioner 312 may bias the sealing portion 310 of conical member 304 against the interior of the fluid container, oftentimes creating a seal. Generally, the components of FIGS. 3A-3D are oriented with a top 305 and a bottom 315. The fluid container 316 may include a neck 324, a shoulder 326, and a body 328.

Referring specifically to FIG. 3A, insertion of the fluid container adapter 300 in the collapsed configuration 320 into the fluid container 316 may include disposing the sealing portion 310 of conical member 304 into an interior of fluid container 316 via an opening 322 in neck 324. In other embodiments, the sealing portion 310 may be inserted into openings in one or more of the neck 324, the shoulder 326, and/or the body 328. The sealing portion 310 may be flexible and collapsible to facilitate insertion into openings in fluid containers with a variety of characteristics (e.g., shapes, sizes, diameters, configurations, depths, position, orientation, and the like).

Referring specifically to FIG. 3B, the sealing portion 310 (in an expanded configuration 320) disposed in the interior 334 of the fluid container adapter 300 may include the sealing portion 310 contacting the interior 332 of the fluid container 316. In various embodiments, the sealing portion 310 may contact one or more interior portions of the fluid container 316 (e.g., neck 324, shoulder 326, and/or body 328). Flexibility of the sealing portion 310 may facilitate transition in between the collapsed configuration 320 and the expanded configuration 330. In several embodiments, the sealing portion 310 may be biased into the expanded configuration 330. For example, shape-memory material may be utilized to bias the sealing portion 310 into the expanded configuration 330. In some embodiments, a material embedded in or disposed on one or more surfaces (e.g., the surface opposite the surface of sealing portion 310 that contacts fluid container 316) may bias the sealing portion 310 into the expanded configuration 330.

Referring specifically to FIG. 3C, the tensioner 312 may be coupled with the threaded portion 308 of the conical member 304 of the fluid container 300. In many embodiments, the tensioner 312 includes a threaded opening to screw onto the threaded portion 308 of conical member 304. Accordingly, the threaded opening of tensioner 312 may correspond (e.g., mate) with the threaded portion 308 of conical member 304. Referring specifically to FIG. 3D, the tensioner 312 may bias the sealing portion 310 of the conical member 304 against the interior 332 of the fluid container 316. The tensioner 312 may contact and apply a force against an exterior surface of the fluid container (e.g., proximate the opening 322) to bias the conical member against the interior 332. In the illustrated embodiment, the sealing portion 310 is biased toward the top 305 of the fluid container 316. In many embodiments, biasing the sealing portion 310 against the interior 332 of fluid container 316 with tensioner 312 may seal an exterior 332 from the interior 332 of the fluid container 316.

Figure 4A:
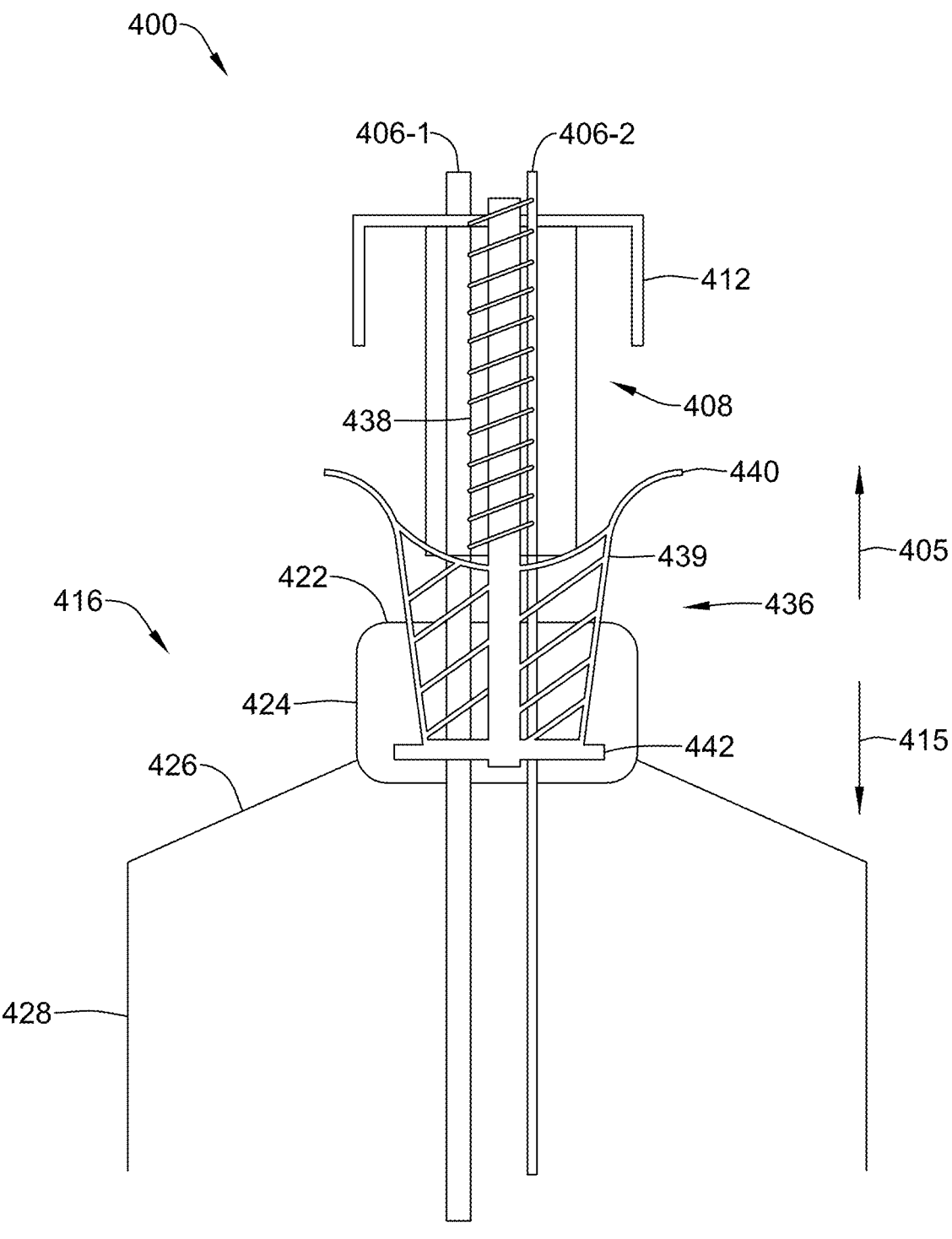
FIGS. 4A-4D illustrate exemplary aspects of a fluid container adapter in conjunction with a fluid container according to one or more embodiments disclosed hereby.
Figure 4B:
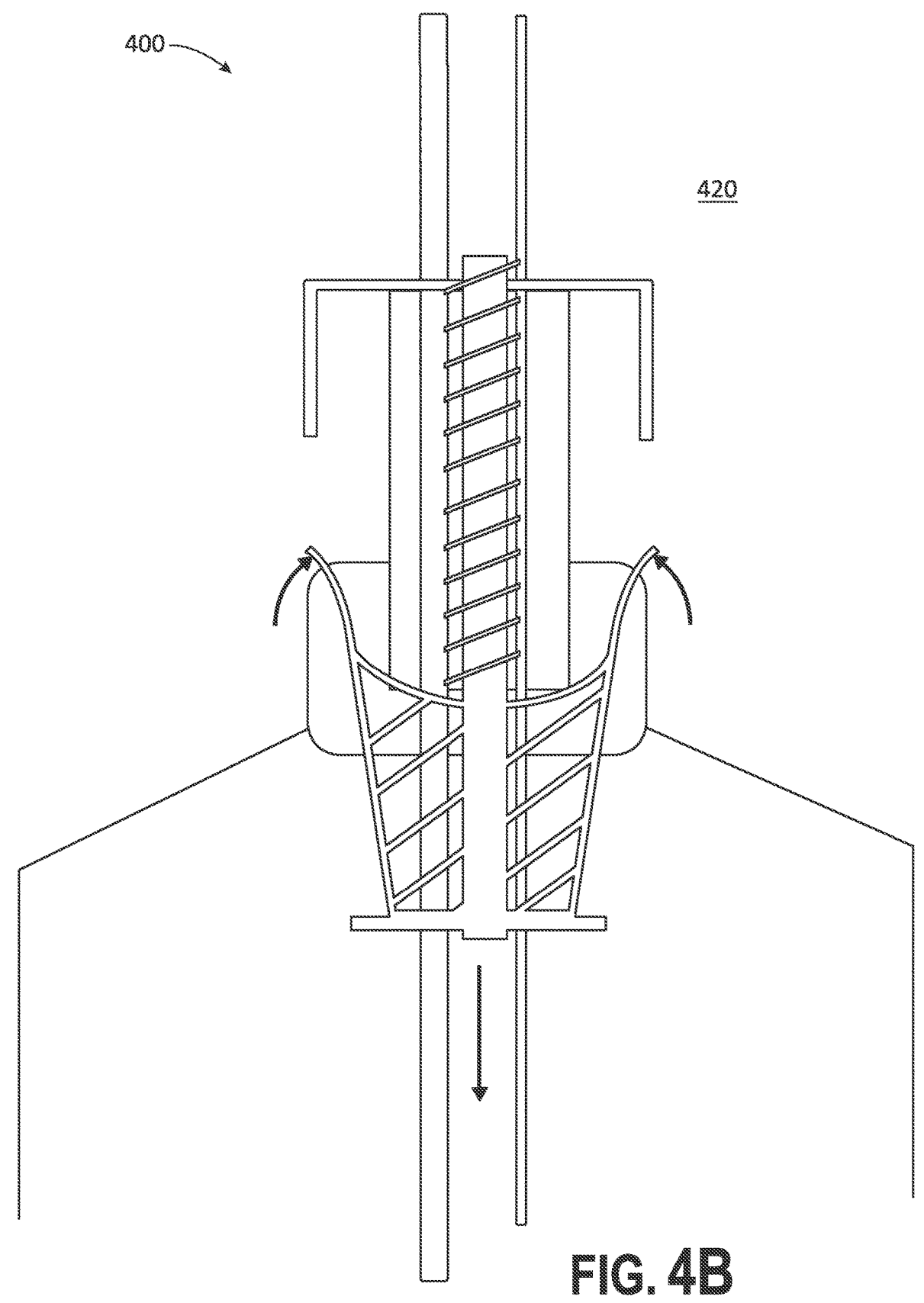
Figure 4C:
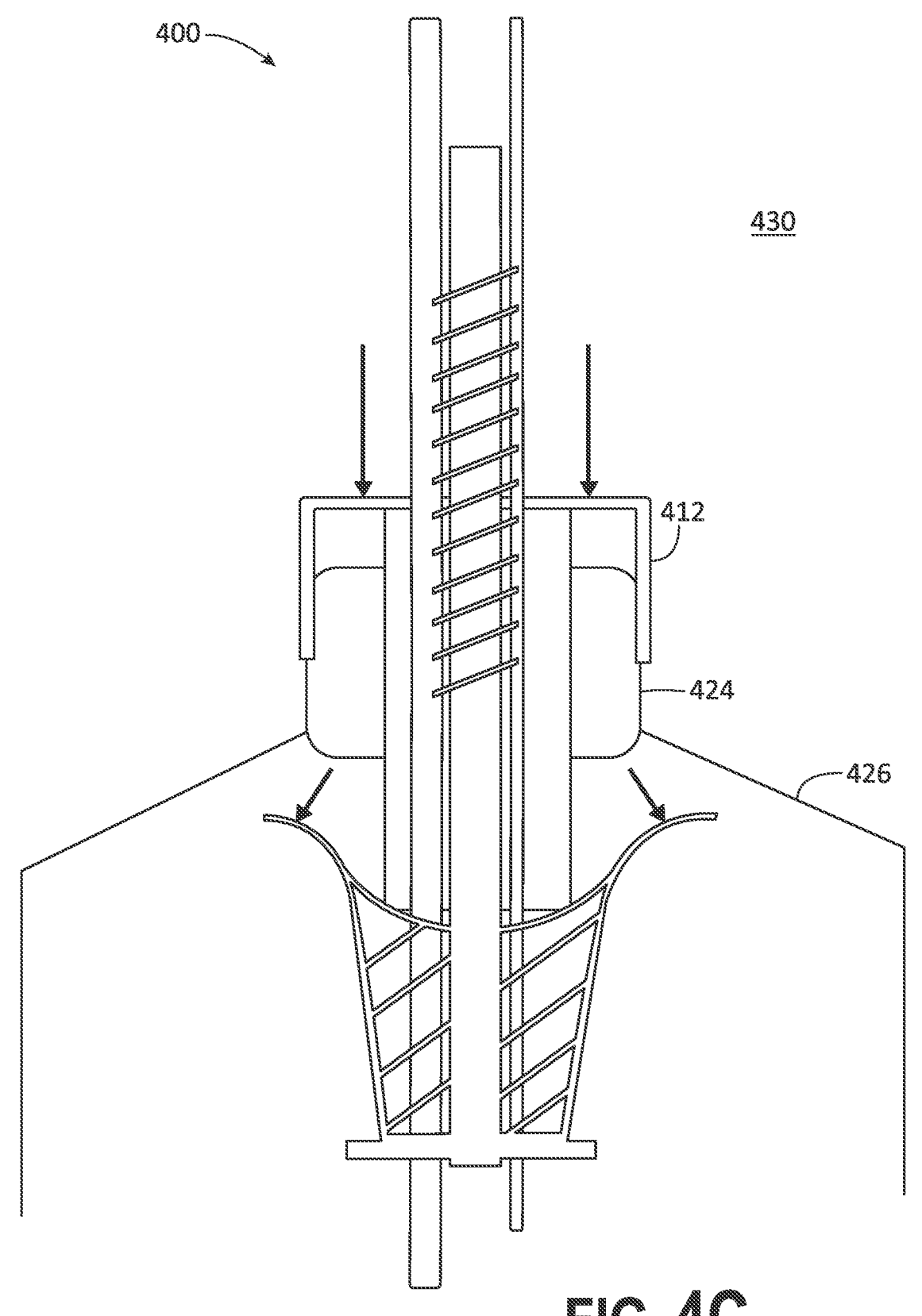
Figure 4D:
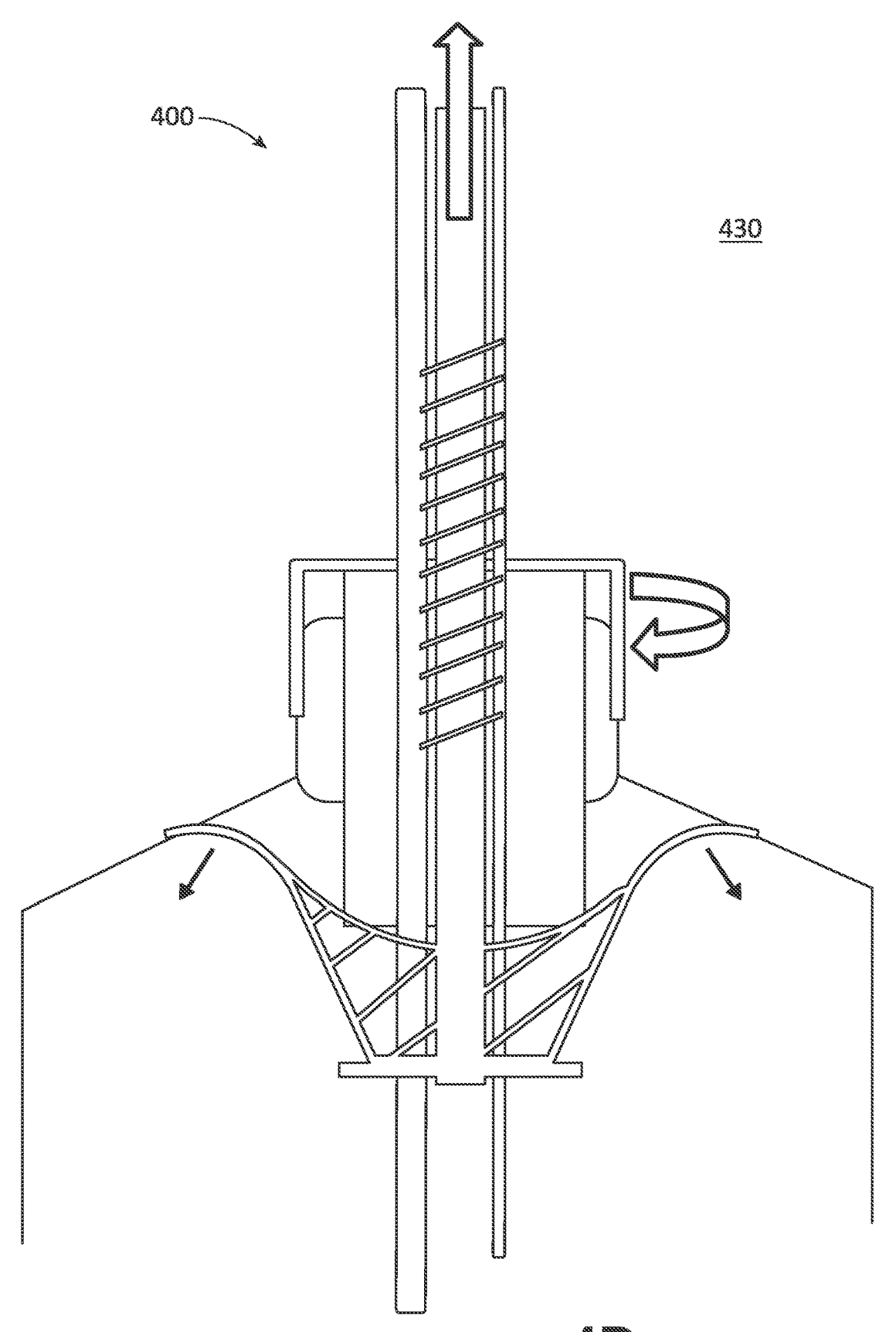

FIGS. 4A-4D illustrate various aspects of a fluid container adapter 400 in conjunction with a fluid container 416 according to one or more embodiments of the present disclosure. More specifically, FIG. 4A illustrates tubes 406-1, 406-2 extending through the fluid container adapter 400 and into the fluid container 416 via opening 422. FIG. 4B illustrates an umbrella seal 436 of the fluid container adapter 400 transitioning to a collapsed configuration 420 during insertion into the fluid container 416. FIG. 4C illustrates the umbrella seal 436 of the fluid container adapter 400 transitioning to an expanded configuration 430 after insertion into the fluid container 416. FIG. 4D illustrates biasing the umbrella seal 436 into contact with an interior the fluid container 416 with tensioner 412. In some embodiments, FIGS. 4A-4D may include one or more components that are the same or similar to one or more other components of the present disclosure. Further, one or more components of FIGS. 4A-4D, or aspects thereof, may be incorporated into other embodiments of the present disclosure without departing from the scope of this disclosure. For example, tensioner 412 of fluid container adapter 400 may be the same or similar to tensioner 312 of fluid container adapter 300. In another example, umbrella seal 436 may be incorporated into fluid container adapter 100 without departing from the scope of this disclosure. Embodiments are not limited in this context.

Fluid container adapter 400 may include tensioner 412, umbrella seal 436, and connecting member 438. In various embodiments, connecting member 438 may extend between the tensioner 412 and the umbrella seal 436. The connecting member 438 may include a threaded portion 408 to facilitate using the tensioner 412 to bias the umbrella seal 436 into contact with the fluid container 416. For example, tensioner

412 may include a threaded opening that corresponds to the threaded portion 408 of connecting member 438. Tubes 406-1, 406-2 extend through the fluid container adapter 400 via passages (not illustrated) extending through one or more components of the fluid container adapter 400, such as tensioner 412 and/or umbrella seal 436 (e.g., via base 442). In several embodiments, the tensioner 412 and the umbrella seal 436 may include one or more axially aligned passages to facilitate fluid communication between a tube and the interior of the fluid container. In many embodiments, the umbrella seal 436 may be inserted into fluid container 416 and the tensioner 412 may bias the umbrella seal 436 against the interior of the fluid container 416, oftentimes creating a seal. Generally, the components of FIGS. 4A-4D are oriented with a top 405 and a bottom 415. The fluid container 416 may include a neck 424, a shoulder 426, and a body 428.

The fluid container adapter 400 may utilize an inverted umbrella style valve (e.g., umbrella seal 436). The umbrella seal 436 may include a base 442 and a skirt 439 with flare 440 extending therefrom. The umbrella seal 436 may transition between a collapsed configuration 420 (see e.g., FIG. 4B) and an expanded configuration 430 (see e.g., FIG. 4C). In several embodiments, the umbrella seal may be biased into the expanded configuration 430. For example, one or more components of the skirt 439 may bias the umbrella seal 436 into the expanded configuration 430. In some such examples, the skirt 439 may include one or more biasing members (e.g., illustrated diagonal lines) constructed from an elastic material.

In FIG. 4A, the base 442 is inserted into the opening 422 of fluid container 416. In various embodiments, the base 442 may be a circular member (e.g., disk) and/or include a circular portion. The outside diameter of the flare 440 is larger than the inner diameter of the opening 422. Accordingly, as illustrated in FIG. 4B, the umbrella seal 436 may transition to the collapsed configuration 420, such as by the skirt 439 and flare 440 deflecting inwards (e.g., towards connecting member 438) when passing through the opening 422 as base 442 extends towards the bottom of the fluid container 416. The umbrella seal 436 may be flexible and collapsible to facilitate insertion into openings in fluid containers with a variety of characteristics (e.g., shapes, sizes, diameters, configurations, depths, position, orientation, and the like).

When the outside diameter of the flare 440 in the expanded configuration 430 is less than the inside diameter of the fluid container 416, the umbrella seal 436 may return to the expanded configuration 430. In some embodiments, the umbrella seal 436 may not fully return to the expanded configuration 430. For example, the umbrella seal 436 may return to a semi-expanded configuration when the interior diameter of the fluid container is less than the outside diameter of the flare 440 in the expanded configuration 430. In such examples, the fluid container adapter 400 may still function properly in the semi-expanded state.

Referring to FIG. 4C, the umbrella seal 436 returns to the expanded configurations 430 once the flare 440 moves below the neck 424 of the fluid container 416. Referring to FIG. 4D, when the umbrella seal 436 is in the expanded state 430, or a semi-expanded state, on the interior of the fluid container 416, tensioner 416 may be utilized to bias the umbrella seal 436 towards the top of the fluid container 416 and cause flare 440 to contact and/or seal with the interior of the fluid container 416. In various embodiments, the biasing occurs when tensioner 412 is screwed onto threaded portion 408 of connecting member 438 and contacts the exterior of the opening 422 as shown in FIG. 4D. Other techniques may be utilized to bias with a tensioner, such as one or more of ratcheting, sliding lock, pull lock, gears, tracks, mating features, and the like.

Figure 5A:
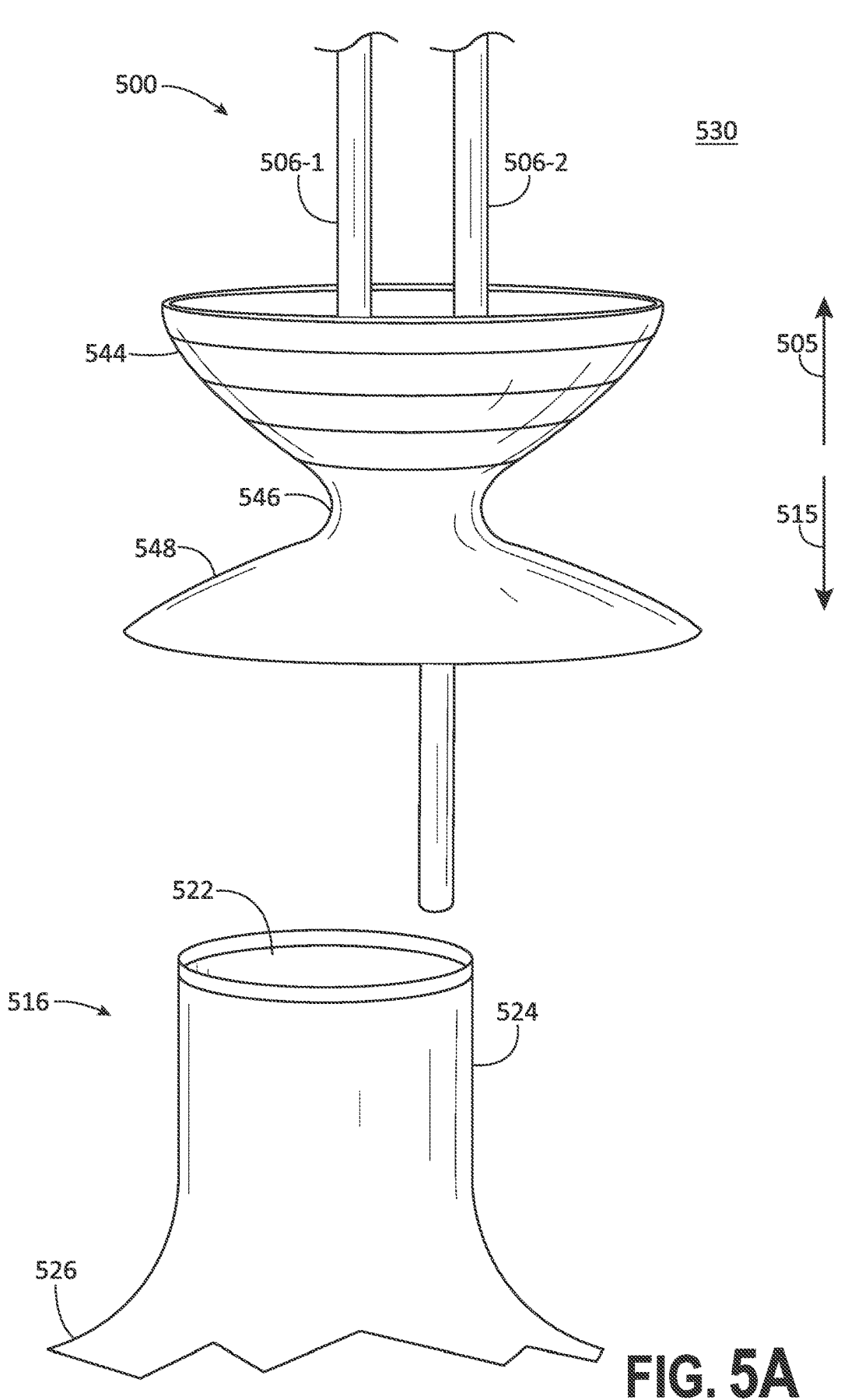
FIGS. 5A-5C illustrate exemplary aspects of a fluid container adapter in conjunction with a fluid container according to one or more embodiments disclosed hereby.
Figure 5B:
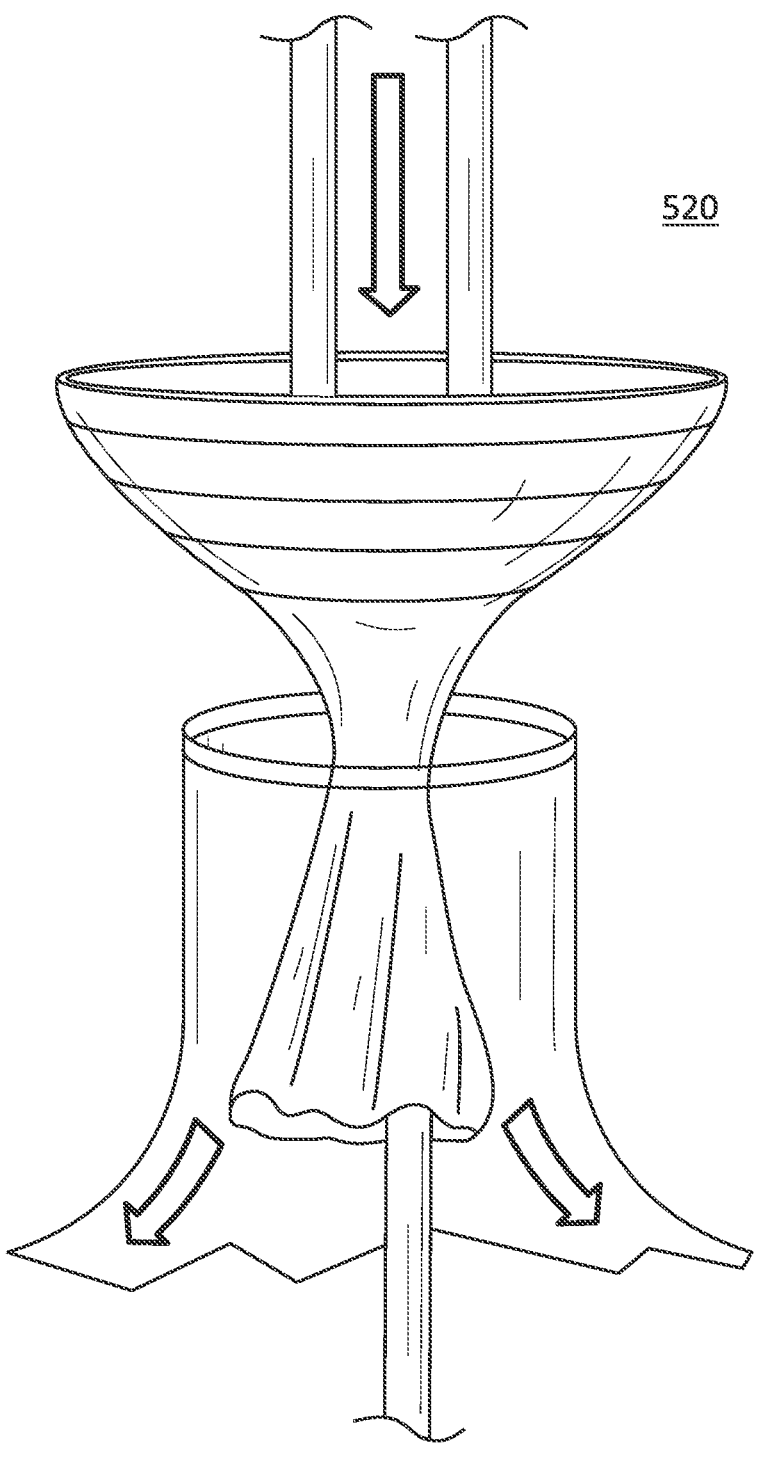
Figure 5C:
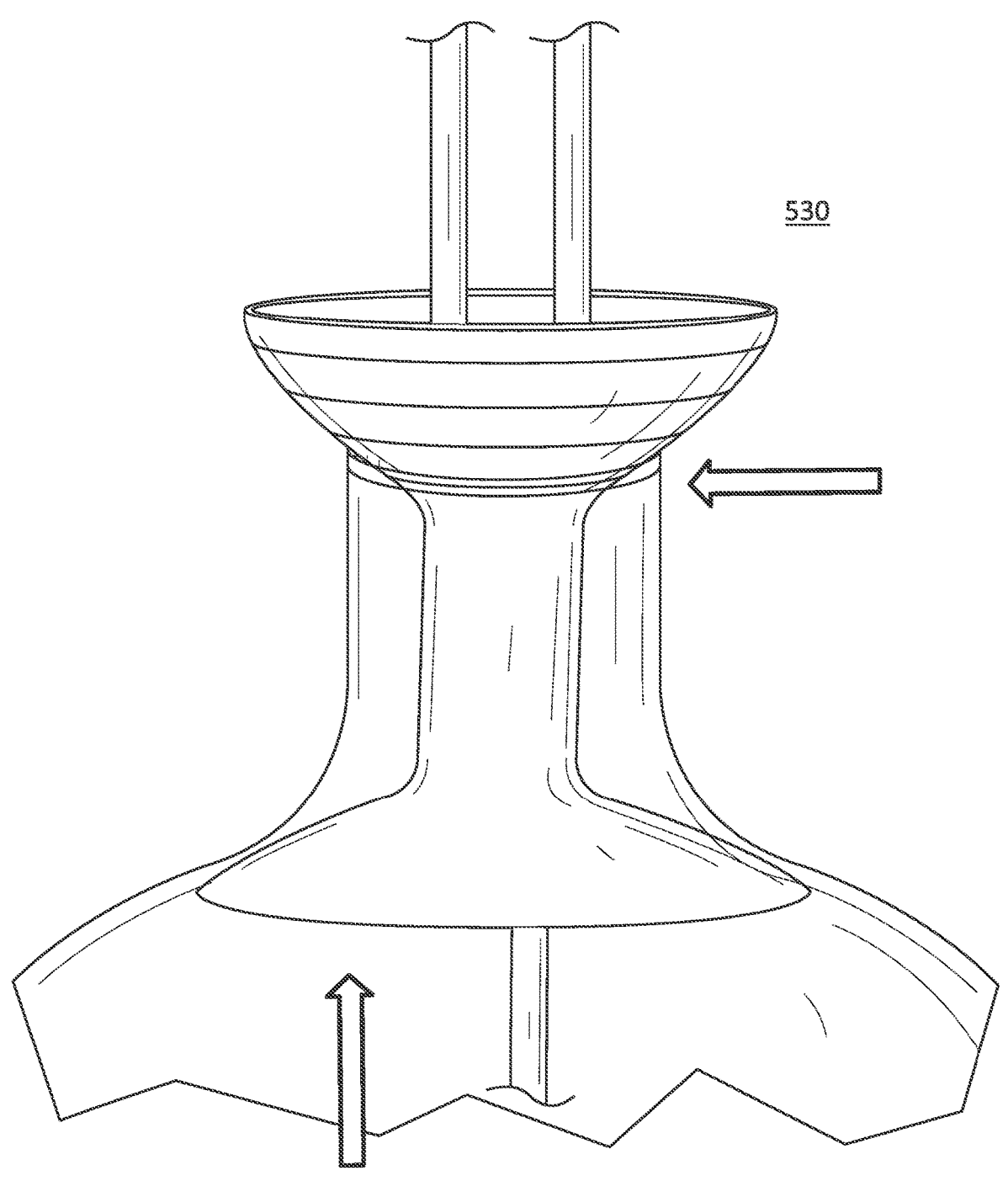

FIGS. 5A-5C illustrate various aspects of a fluid container adapter 500 in conjunction with a fluid container 516 according to one or more embodiments of the present disclosure. More specifically, FIG. 5A illustrates fluid container adapter 500 having a conical member 504 with a plugging portion 544, a necking portion 546, and a sealing portion 548; tube 506-1 extending into fluid container adapter 500; and tube 506-2 extending through fluid container adapter 500 and toward opening 522 in fluid container 516. FIG. 5B illustrates the sealing portion 548 of the conical member 504 in a collapsed configuration 520. FIG. 5C illustrates the sealing portion 548 of the conical member 504 in an expanded configuration 530. In some embodiments, FIGS. 5A-5C may include one or more components that are the same or similar to one or more other components of the present disclosure. Further, one or more components of FIGS. 5A-5C, or aspects thereof, may be incorporated into other embodiments of the present disclosure without departing from the scope of this disclosure. For example, sealing portion 548 of conical member 504 may be the same or similar to sealing portion 210 of conical member 204. Embodiments are not limited in this context.

In the illustrated embodiment, conical member 504 includes an hourglass shape with the plugging portion 544 comprising the top part of the hourglass shape, the sealing portion 548 comprising the bottom part of the hourglass shape, and the necking portion 546 comprising the junction of the top and bottom parts of the hourglass shape.

As previously mentioned, sealing portion 548 may transition between a collapsed configuration 520 and an expanded configuration 530. In the absence of external force, the sealing portion 548 may be biased into the expanded configuration. In some embodiments, one or more cables and/or strings may be utilized to transition sealing portion 548 from the expanded configuration 530 to the collapsed configuration. In some such embodiments, the cables/strings may be disposed within one or more internal passages in the conical member 504.

In many embodiments, the plugging portion 544 and/or the necking portion 546 may bias the sealing portion 548 towards the top of the fluid container 516. In many such embodiments, the sealing portion 548 may be biased into contact with shoulder 526 and/or neck 524 of fluid container 516. In the illustrated embodiment, plugging portion 544 includes a plurality of latitudinal features. The latitudinal features may include steps or ribs, such as ribs to provide the plugging portion 544 with grip at the opening 522. In several embodiments, the sealing portion 548 collapses to a smaller diameter than the plugging portion 544.

In some embodiments, the plugging portion 544 and/or necking portion 546 may comprise a lower durometer material than the sealing portion 548. In some such embodiments, the low durometer material (e.g., silicon) may allow the plugging portion 544 and/or necking portion 546 to stretch or compress enough to facilitate transition of the sealing portion 548 back to the expanded configuration 530 when inserted into the interior of the fluid container 516. When the plugging portion 544 and/or necking portion 546 draw the sealing portion 548 upward until the sealing portion 548 creates a seal against the interior of fluid container 516 (e.g., shoulder 526).

In one or more embodiments, the radial force of the conical member 404 may cause the sealing portion 548 to remain distended. In one or more such embodiments, the sealing portion 548 may include a flexible membrane to facilitate conformation with a variety of bottle shapes. In embodiments in which the fluid container 516 is pressurized, the internal pressure may strengthen the seal. In embodiments in which the fluid container is not pressurized, the fluid container adapter 500 may allow air into the bottle. In some such embodiments, the neck portion 446 may be maintained at ambient temperature. After use, fluid container adapters disclosed hereby (e.g., fluid container adapter 500) may be easily removed from the fluid container.

Figure 6:
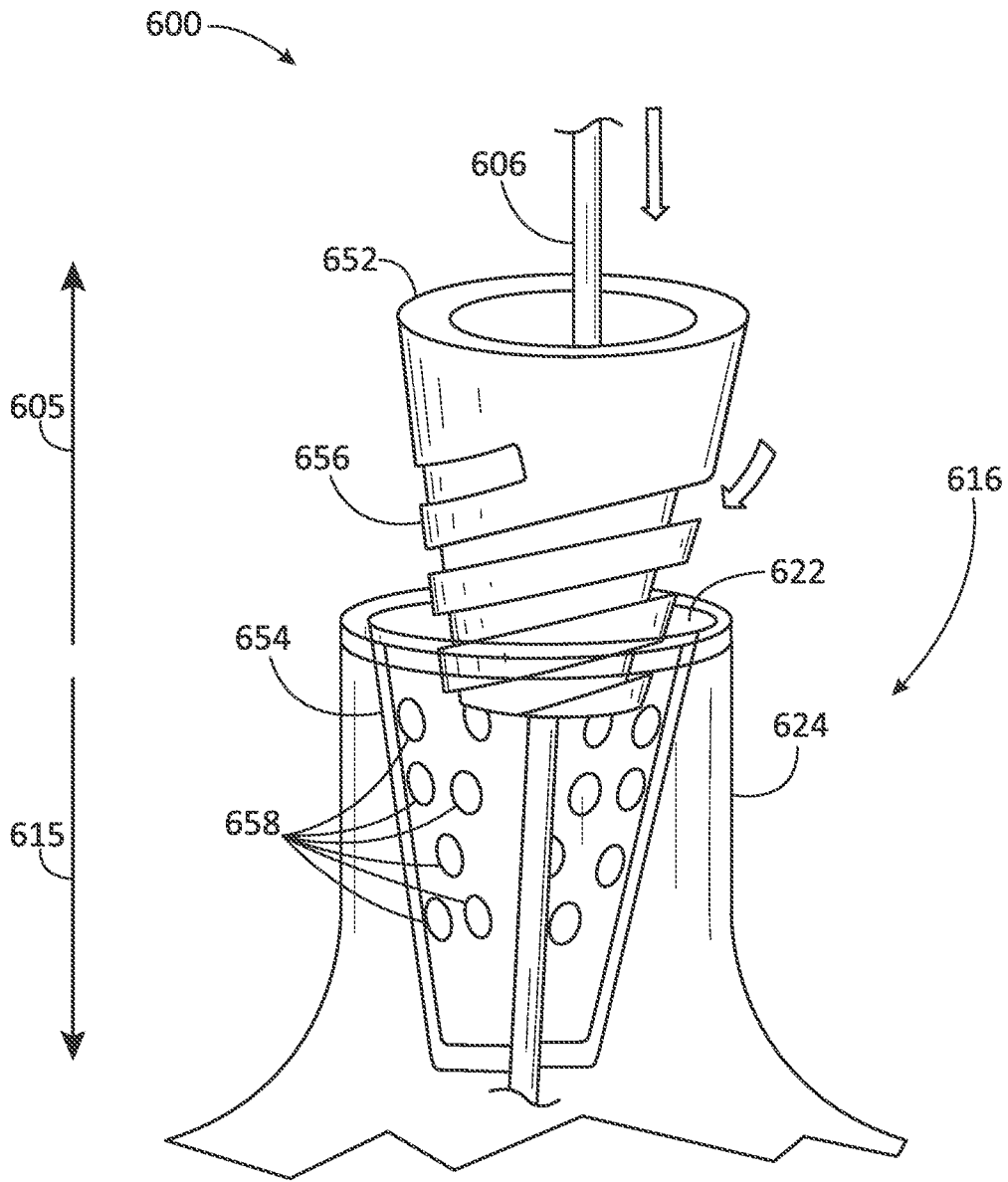
FIG. 6 illustrate exemplary aspects of a fluid container adapter in conjunction with a fluid container according to one or more embodiments disclosed hereby.

FIG. 6 illustrates exemplary aspects of a fluid container adapter 600 in conjunction with a fluid container 616 according to one or more embodiments of the present disclosure. In the illustrated embodiment, fluid container adapter 600 couples to fluid container 616 and places tube 606 in fluid communication with an interior of the fluid container 616. In some embodiments, FIG. 6 may include one or more components that are the same or similar to one or more other components of the present disclosure. Further, one or more components of FIG. 6, or aspects thereof, may be incorporated into other embodiments of the present disclosure without departing from the scope of this disclosure. For example, tube 606 may be the same or similar to one or more tubes in tube set 106. The components of FIG. 6 are oriented with a top 605 and a bottom 615. Embodiments are not limited in this context.

Fluid container adapter 600 includes an inner member 652 with ribs 656 and an outer member 654 with internal features 658. In various embodiments, the inner member 652 is configured to fit into the outer member 654. In various such embodiments, the inner and outer members 652, 654 have the same shape (e.g., cone or plug) and/or taper. In some embodiments, the outer member 654 may be semiflexible and conformable to the shape of an interior portion of the fluid container 616 (e.g., neck 624). The internal features 658 may have a higher durometer than the conical structure of the outer member 654. Further, the internal features 658 may be raised to catch the ribs 656 of the inner member 652.

In some embodiments, tube 606 may be attached proximate the bottom of the outer member 654. In some such embodiments, tube 606 may comprise a portion of an air catheter. In one or more embodiments, tube 606 may be attached to a base at the bottom of the outer member 654. The base of the outer member 654 may be at the bottom end of the taper. In some embodiments, the base may be a circular member (e.g., disk) and/or include a circular portion. The inner member 652 may comprise a higher durometer material than the outer member 654. In various embodiments, the inner member 652 may include a passage that allows it to ride freely on the tube 606.

More generally, the outer member 654 is configured to be inserted into an opening 622 of the fluid container 616. In the illustrated embodiments, the opening 622 is in the neck 624 of the fluid container 616. When the inner member 652 is inserted into the outer member 654 and turned in a first direction the ribs 656 may interface with the internal features 658 to pull the inner member 652 toward the bottom of the outer member 654. Further, pulling the inner member 652 toward the bottom of the outer member 654 applies a radial force to the outer member 654 and causes the outer member 654 to create a seal with the interior of the neck 624. Similarly, turning the inner member 652 in a second direction, opposite the first direction, may reverse the seal and facilitate remove of the fluid container adapter 600 from fluid container 616.

As previously mentioned, various embodiments of the present disclosure include fluid container enclosures that widen the scope of compatibility to a variety of different fluid container designs and/or functionality types, such as insufflation and irrigation. In many embodiments, one or more fluid container enclosures of the present disclosure may provide an efficient, safe, and effective way to couple with and gain access to the contents of a multitude of fluid container designs. Enabling fluid container enclosures to be compatible with different fluid container designs allows manufacturers of tubing sets to offer products that are more adaptable. Further, enabling fluid container enclosures to be compatible with different fluid container designs can simplify product acquisition and stocking by health care facilities.

For example, enclosure systems according to some embodiments may be used with a wide variety of fluid container port, opening, or neck dimensions, such as an opening diameter and/or thread configuration (for instance, Glass Packaging Institute (GPI) thread finish, "H" dimension, thread distance, thread dimensions, and/or the like), thread pitch, outer diameter (OD) of port or neck (OD port), OD of threads (OD thread), thread width, and/or the like. In addition, enclosure systems according to some embodiments may be used on fluid containers made by various manufacturers.

For example, in some embodiments, an enclosure system may include a single cap that is capable of being installed on containers having an opening size (e.g., neck OD, not including threads) of about 10 mm, about 20 mm, about 30 mm, about 40 cm mm about 50 mm, about 100 mm, about 200 mm, and any value or range between any two of these values (including endpoints). In some embodiments, an enclosure system may include a single cap that is capable of being installed on containers having an opening size (e.g., neck OD, not including threads) of about 30 mm, about 30.4 mm, about 31 mm, about 32 mm, about 32.2 mm to about 32.9 mm, about 33 mm, about 33.6 mm, about 34 mm, about 35 mm, about 40 mm, and any value or range between any two of these values (including endpoints).

In some embodiments, an enclosure system may include a single cap that is capable of being installed on containers having a total opening size (e.g., neck OD including threads) of about 10 mm, about 20 mm, about 30 mm, about 40 cm mm about 50 mm, about 100 mm, about 200 mm, and any value or range between any two of these values (including endpoints). In some embodiments, an enclosure system may include a single cap that is capable of being installed on containers having a total opening size (e.g., neck OD including threads) of about 30 mm, about 31 mm, about 32 mm, about 33 mm, about 33.2 mm, about 34 mm, about 35 mm, about 35.75 mm, about 36 mm, about 36.26 mm, about 40 mm, and any value or range between any two of these values (including endpoints).

In some embodiments, an enclosure system may include a single cap that is capable of being installed on containers having a thread width of about 0.5 mm, about 1 mm, about 2 mm, about 3 mm, about 4 mm, about 5 mm, about 10 mm, and any value or range between any two of these values (including endpoints). In some embodiments, an enclosure system may include a single cap that is capable of being installed on containers having a thread width of about 1 mm, about 1.83 mm, about 2 mm, about 2.4 mm, about 2.66 mm, about 3 mm, and any value or range between any two of these values (including endpoints).

In some embodiments, an enclosure system may include a single cap that is capable of being installed on containers having a thread pitch of about 1 mm, about 2 mm, about 3 mm, about 4 mm, about 5 mm, about 6 mm, about 7 mm, about 8 mm, about 9 mm, about 10 mm, and any value or range between any two of these values (including endpoints). In some embodiments, an enclosure system may include a single cap that is capable of being installed on containers having a thread pitch of about 3 mm, about 3.94 mm, about 4 mm, about 4.23 mm, about 4.25 mm, about 5 mm, and any value or range between any two of these values (including endpoints).

In some embodiments, an enclosure system may include a single cap that is capable of being installed on a fluid container having a GPI thread finish of 350, 400, 410, 415, 425, 430, 450, and any value or range between any two of these values (including endpoints).

In various embodiments, an enclosure system may include a single cap that is capable of being installed on different types of fluid container openings or necks. For example, a cap of an enclosure system according to some embodiments may be installed on (and form a seal with) fluid container openings/necks with different dimensions. In some embodiments, an enclosure system may include a single cap that is capable of being installed on a plurality of fluid container necks having a OD thread difference (Δ OD thread) (i.e., the difference between an OD thread of the smallest OD thread neck and the largest OD thread neck) of about 0.25 mm, about 0.5 mm, about 1 mm, about 1.5 mm, about 2 mm, about 3 mm, about 4 mm, about 5 mm, about 10 mm, and any value or range between any two of these values (including endpoints). In various embodiments, an enclosure system may include a single cap that is capable of being installed on a plurality of fluid container openings having a OD opening difference (Δ OD opening) (i.e., the difference between an OD opening of the neck with the smallest OD opening and the port with the largest OD opening) of about 0.25 mm, about 0.5 mm, about 1 mm, about 1.5 mm, about 2 mm, about 3 mm, about 4 mm, about 5 mm, about 10 mm, and any value or range between any two of these values (including endpoints).

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method of the present disclosure without departing from the concept, spirit and scope of the disclosure. All such similar substitutes and modifications apparent to those skilled in the art are deemed to be within the spirit, scope and concept of the disclosure as defined by the appended claims.

What is claimed is:

1. An apparatus, comprising:
   a conical member comprising a connector portion, a sealing portion, and one or more passages extending from the connector portion to the sealing portion, the sealing portion comprising a collapsed configuration for insertion into a fluid container and an expanded configuration for sealing with an interior of the fluid container; and
   a tensioner with a coupler, the tensioner configured to couple with the connector portion of the conical member, contact an exterior of the fluid container, and bias the sealing portion into contact with the interior of the fluid container.

2. The apparatus of claim 1, wherein each of the one or more passages are configured to facilitate fluid communication between a tube and the interior of the fluid container.

3. The apparatus of claim 1, wherein the sealing portion comprises an elastomeric structure to bias the sealing portion into the expanded configuration.

4. The apparatus of claim 1, wherein an outer diameter of the sealing portion of the conical member changes non-linearly.

5. The apparatus of claim 1, wherein the connector portion includes a top of the conical member, the sealing portion comprises a bottom of the conical member, and the connector portion abuts the sealing portion at a transition of the conical member.

6. The apparatus of claim 5, wherein the top of the conical member has a first diameter, the transition of the conical member has a second diameter, and the bottom of the conical member has a third diameter.

7. The apparatus of claim 6, wherein the first and second diameters are smaller than the third diameter.

8. The apparatus of claim 1, wherein the sealing portion of the conical member in the collapsed configuration is configured for insertion into the fluid container via an opening in a neck of the fluid container and the tensioner is configured to seal with the opening in the neck of the fluid container when fastened onto the connector portion.

9. The apparatus of claim 8, wherein the tensioner comprises a first side and a second side, the first side including a rigid material and the second side including a flexible material configured to seal with the opening in the neck of the fluid container.

10. The apparatus of claim 1, wherein the connector portion of the conical member comprises a rigid material and the sealing portion of the conical member comprises a flexible material.

11. The apparatus of claim 10, wherein the tensioner comprises the rigid material.

12. The apparatus of claim 1, wherein the tensioner comprises a rigid disc.

13. The apparatus of claim 1, wherein the sealing portion is configured to conform to a shape of the interior of the fluid container in the expanded configuration.

14. A method, comprising:

transitioning a sealing portion of a conical member from an expanded configuration to a collapsed configuration, the conical member comprising a connector portion, the sealing portion, and one or more passages extending from the connector portion to the sealing portion, wherein the sealing portion is biased to the expanded configuration;

inserting the sealing portion in the collapsed configuration into an interior of a fluid container, wherein when the sealing portion is in the interior of the fluid container, the sealing portion returns to the expanded configuration and the connector portion extends out of the fluid container; and biasing an exterior surface of the sealing portion into contact with the interior of the fluid container while allowing fluid from the interior of the fluid container to pass through the one or more passages.

15. The method of claim 14, comprising fastening a tensioner onto the connector portion of the conical member to bias the sealing portion into contact with the interior of the fluid container.

* * * * *